(12) United States Patent
Lao et al.

(10) Patent No.: US 8,697,919 B2
(45) Date of Patent: Apr. 15, 2014

(54) 1-METHOXYL-2, 6, 10-TRIMETHYL-1, 3, 5, 9-UNDEC-TETRAENE, AND PREPARATION METHOD AND USES THEREOF

(75) Inventors: Xuejun Lao, Zhejiang (CN); Runpu Shen, Zhejiang (CN); Weidong Ye, Zhejiang (CN); Xiaohua Song, Zhejiang (CN); Luo Liu, Zhejiang (CN); Chunlei Wu, Zhejiang (CN); Xiongsheng Sun, Zhejiang (CN); Siping Hu, Zhejiang (CN)

(73) Assignees: Zhejiang Medicine Co., Ltd., Xinchang Pharmaceutical Factory, Xinchang, Shaoxng, Zhejiang (CN); University of Shaoxing, Shaoxing, Zhejiang (CN)

( * ) Notice: Subject to any disclaimer, the term of this patent is extended or adjusted under 35 U.S.C. 154(b) by 0 days.

(21) Appl. No.: 13/639,852

(22) PCT Filed: Apr. 6, 2011

(86) PCT No.: PCT/CN2011/072472
§ 371 (c)(1),
(2), (4) Date: Oct. 8, 2012

(87) PCT Pub. No.: WO2011/124130
PCT Pub. Date: Oct. 13, 2011

(65) Prior Publication Data
US 2013/0046114 A1 Feb. 21, 2013

(51) Int. Cl.
*C07C 45/42* (2006.01)
*C07C 41/30* (2006.01)
*C07C 43/15* (2006.01)

(52) U.S. Cl.
USPC .......................................... 568/485; 568/687

(58) Field of Classification Search
USPC .................................... 568/485, 687
See application file for complete search history.

(56) References Cited

U.S. PATENT DOCUMENTS 4,675,451 A * 6/1987 Andrade et al. .............. 568/486
5,973,179 A * 10/1999 Babler et al. ..................... 558/83

OTHER PUBLICATIONS

Valla et al. New Synthesis of Retinal and its Acyclic Analog gamma-Retinal by and Extended Aldol Reaction with a C6 Buliding Block that Incorporates a C5 Unit after Decarboxylation. A Formal Route to Lycopene and Beta-Carotene. Helvetica Chemica Acta, 2007, vol. 90, pp. 512-520.*

* cited by examiner

*Primary Examiner* — Sikarl Witherspoon
(74) *Attorney, Agent, or Firm* — Global IP Services; Tianhua Gu

(57) ABSTRACT

The invention discloses an intermediate 1-methoxyl-2,6,10-trimethyl-1,3,5, 9-undec-tetraene, and a preparation method and uses thereof. In the synthesis method for the current lycopene intermediate 2-pos double bond C-14 aldehyde (2,6,10-trimethyl-2,5,9-undecatriene-1-aldehyde), expensive methyl iodide, polluting dimethyl sulphide and dangerous strong base are needed, so that the method is hardly applied to industrial production. The invention provides a new compound 1-methoxyl-2,6,10-trimethyl-1,3,5,9-undec-tetraene, and pure 2-pos double bond C-14 aldehyde can be prepared by hydrolyzing and refining the compound. The synthetic route is simplified and the great suitability for industrial production is achieved.

13 Claims, No Drawings

1-METHOXYL-2, 6, 10-TRIMETHYL-1, 3, 5, 9-UNDEC-TETRAENE, AND PREPARATION METHOD AND USES THEREOF

CROSS REFERENCE TO RELATED PATENT APPLICATION

The present application is the US national stage of PCT/CN2011/072472 filed on Apr. 6, 2011, which claims the priority of the Chinese patent application No. 201010139797.5 filed on Apr. 6, 2010, which application is incorporated herein by reference.

TECHNICAL FIELD

The invention relates to an intermediate 1-methoxyl-2,6,10-trimethyl-1,3,5,9-undec-tetraene, and a preparation method and uses thereof.

BACKGROUND

In nature, there are approximately 600 types of carotenoids, but only six of them can be used for industrial production by manufacturers including Roche Company and BASF Company, and lycopene, as an important product among them, plays a key role in free radical removal, anti-aging, tumor inhibition, treatment for heart disease and the like and is widely applied to drugs, food additives and feed additives. Roche Company has developed a Wittig reaction-featured synthetic route in which expensive and toxic raw material triphenylphosphine is used, and triphenylphosphine is used in a variety of other early synthesis methods as well.

Babler J. H. et al. reported a novel Wittig-Horner reaction-featured method for the synthesis of lycopene in WO 0031086, in which 3,7,11-trimethyl-2,4,6,10-tetraene-dodecyl diethyl phosphonate (5) is used as key intermediate and condensed with decadialdehyde (8) under the catalysis of base to prepare lycopene, and the total synthesis process is as follows:

At first, pseudoionone (2) reacts with acetylene anion to obtain tertiary alcohol (7) (3,7,11-trimethyl-4,6,10-dodecyl triene-1-alkynyl-3-alcohol):

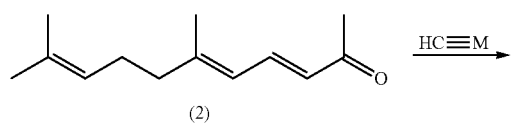

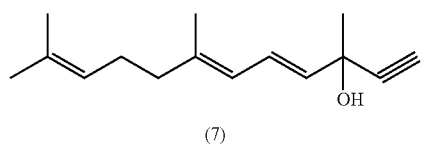

Then, the tertiary alcohol (7) reacts with diethyl chlorophosphite to obtain propadiene pentadec-carbon phosphonate (6) (3,7,11-trimethyl-1,2,4,6,10-pentaene-dodecyl diethyl phosphonate):

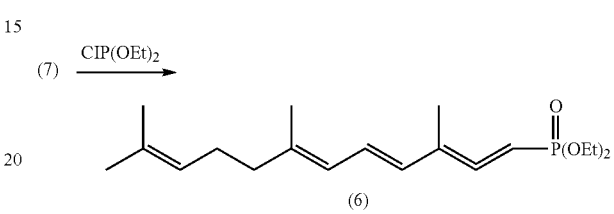

Afterwards, (6) is partially reduced and converted into pentadec-carbon phosphonate (5) (3,7,11-trimethyl-2,4,6,10-tetraene-dodecyl diethyl phosphonate)

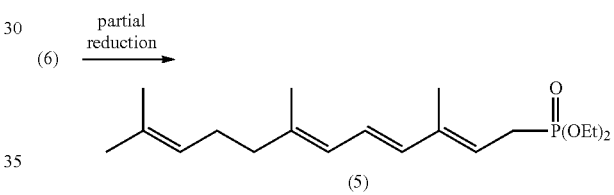

Finally, pentadec-carbon phosphonate (5) and decadialdehyde (8) (2,7-dimethyl-2,4,6-trieneoctane-1,8-dialdehyde) are condensed under the catalysis of base to prepare lycopene (1):

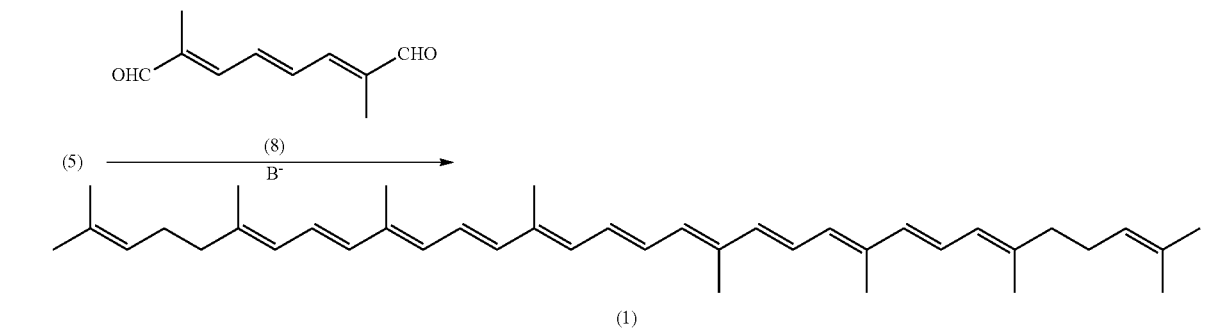

In the method above, the new compound 2,4,6,10-tetra-double bond pentadec-carbon phosphonate (5) is used as key intermediate, which avoids the use of triphenylphosphine; besides, with the pseudoionone as raw material, the target product lycopene can be obtained only by four reactions, so the route is simple and convenient and tremendous progress is achieved compared with previous methods. However, this route has some problems: first, it is difficult, to a certain extent, to obtain (6) by means of the reaction between (7) and dialkyl chlorophosphite; and second, it is difficult to grasp the reduction technology for selectively reducing (6) into (5).

SHEN Runbo et al. have recently reported a new process in their research findings (patent application number: 201010120583.3), in which a compound 1,3,6,10-tetra-double bond pentadec-carbon phosphonate (4) (3,7,11-trimethyl-1,3,6,10-tetraene-dodecyl diethyl phosphonate) and the decadialdehyde (8) are subjected to condensation reaction to obtain lycopene (1), and the process has the synthetic route below:

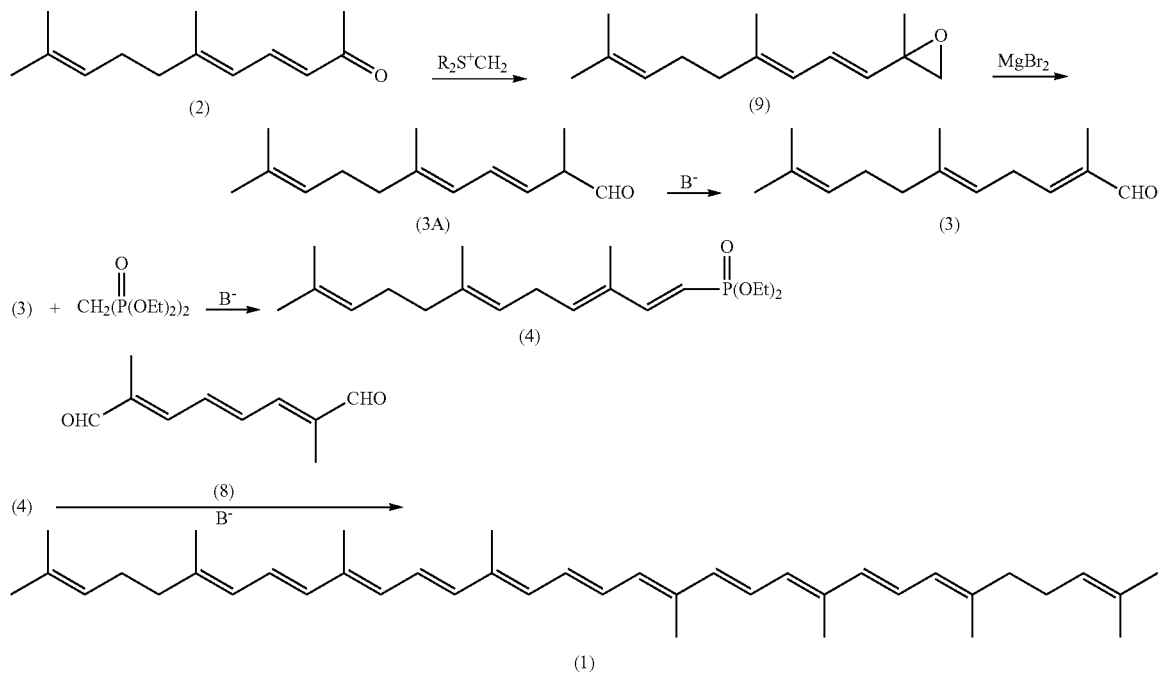

The synthesis method for its key intermediate C-14 aldehyde (3) (2,6,10-trimethyl-2,5,9-undecane triene-1-aldehyde) is described in U.S. Pat. No. 4,000,131, in which pseudoionone (2) reacts with sulfonium chloride to obtain epoxide (9), ring opening is then performed under catalysis to obtain 3-pos double bond C-14 aldehyde (3A) (2,6,10-trimethyl-3,5,9-undecane triene-1-aldehyde), and finally, 3-pos double bond C-14 aldehyde (3A) is subjected to base catalysis and rearrangement to obtain 2-pos double bond C-14 aldehyde (3). Expensive methyl iodide, polluting dimethyl sulphide and dangerous strong base, i.e. DMSO sodium salt, are needed in this method, so that the method is hardly applied to industrial production.

SUMMARY OF THE INVENTION

The technical problem to be solved by the invention is to overcome the defects in the prior art and provide a new compound 1-methoxyl-2,6,10-trimethyl-1,3,5,9-undec-tetraene, and pure 2-pos double bond C-14 aldehyde can be prepared by hydrolyzing and refining the compound. The synthetic route is simplified and great suitability for industrial production is achieved.

The new compound 1-methoxyl-2,6,10-trimethyl-1,3,5,9-undec-tetraene provided by the invention, C-14 enol ether for short, has the structural formula below:

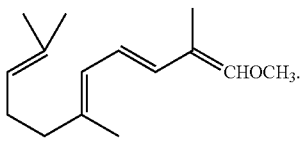

A preparation method of the C-14 enol ether comprises the following steps:

1) C-4 phosphate ester, shown as Formula (6), is subjected to rearrangement dissociation reaction under the protection of inert gas and at the presence of organic solvent and base, wherein the reaction temperature is from −40° C. to 30° C.;

2) citral, shown as Formula (5), is then added to the substance derived from the step 1) to perform Wittig-Horner condensation reaction at the presence of base and organic solvent, thus C-14 enol ether shown as Formula (7) is obtained, wherein the reaction temperature is from −40° C. to 30° C. and the synthetic route is as follows:

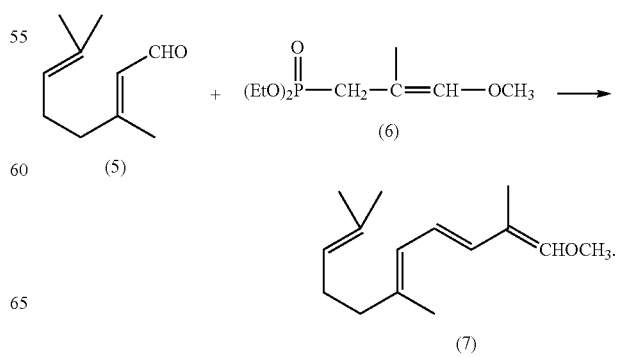

The condensation reaction is performed at the presence of base. The base may be organic base, such as alkali metal salt of alcohols or lithium alkylide, strong bases like sodium alcoholate, sodium tert-butoxide, potassium tert-butoxide and butyl lithium are preferred, and other strong bases are acceptable due to no particular restriction.

The molar weight of base is 1.0-1.2 times as much as that of C-4 phosphate ester (6), preferably 1.02-1.1 times. The molar weight of citral (5) is 0.8-1.2 times as much as that of C-4 phosphate ester (6), preferably 0.9-1.0 times.

The reaction raw material above, i.e. C-4 phosphate ester (6), is either commercially available, or can be prepared in accordance with relevant documents (Bulletin de la Societe Chimique de France, (11), 4186-94; 1967)

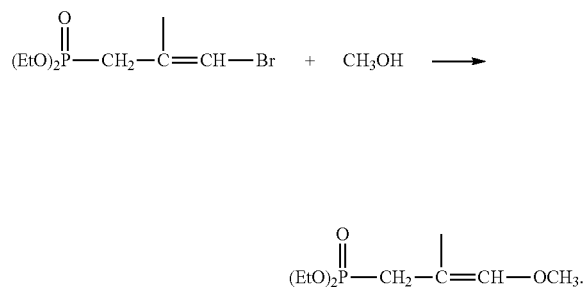

In the above condensation reaction, the reaction raw material C-4 phosphate ester (6) and the base are firstly subjected to rearrangement dissociation reaction to form corresponding carbanions, and then the reaction raw material citral (5) is added for condensation reaction; this way is beneficial not only for the sufficient dissociation of the raw material C-4 phosphate ester (6) into carbanions, but also for controlling the reaction better.

The temperature for the rearrangement dissociation reaction and the condensation reaction of C-4 phosphate ester (6) is −40° C. to 30° C., preferably −20° C. to 10° C.

The organic solvent above is any of or the mixture of more than two of ether solvent, dipolar aprotic solvent, aromatic hydrocarbon solvent and alkane solvent, the ether solvent is ether, tetrahydrofuran or ethylene glycol dimethyl ether, the dipolar aprotic solvent is dimethyl formamide DMF, dimethyl sulfoxide DMSO or hexamethylphosphoric triamide HMPTA, the aromatic hydrocarbon solvent is methylbenzene and the like, and the alkane solvent is n-hexane and the like.

Upon the completion of condensation reaction, water and organic solvent are added for the purpose of layering, a byproduct, i.e. diethyl phosphate sodium salt, is dissolved in water and a product, i.e. C-14 enol ether (7), exists in organic phase, and the target product, i.e. C-14 enol ether (7), can be obtained by removing the solvent in a manner of organic phase distillation.

A method for preparing lycopene intermediate 2-pos double bond C-14 aldehyde from the C-14 enol ether comprises the following steps:

step 1), C-14 enol ether, acid catalyst, water and homogeneous phase solvent are mixed for hydrolysis under the protection of nitrogen in order to obtain a crude product mixture containing 2-pos double bond C-14 aldehyde (3) and 3-position double bond C-14 aldehyde (3A), and the reaction route is as follows:

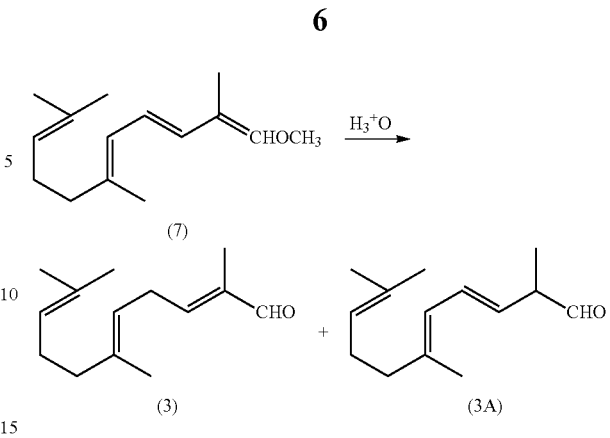

step 2), upon the completion of hydrolysis, sodium bicarbonate aqueous solution is firstly added to adjust the reaction system to be neutral, solvent is then distilled out under reduced pressure, a water-immiscible organic solvent is added for extraction, layering is performed and crude product of C-14 aldehyde is then obtained by drying the solvent by distillation at organic layer, the crude product contains a small amount of 3-pos double bond C-14 aldehyde (3A), a large amount of 2-pos double bond C-14 aldehyde (3) and some other impurities, and pure 2-pos double bond C-14 aldehyde (3) needs to be prepared by refining, which aims at removal of 3-pos double bond C-14 aldehyde (3A).

The acid catalyst that can be used in the hydrolysis of C-14 enol ether (7) is sulfuric acid, p-toluenesulfonic acid, trifluoroacetic acid or aminosulfonic acid due to no particular restriction, the homogeneous phase solvent may be tetrahydrofuran or acetone, etc. The amount of the acid catalyst is 5-10% of the weight of C-14 enol ether (7); the amount of water is 1-3 times as much as the weight of C-14 enol ether (7); the addition amount of the homogeneous phase solvent is 5-10 times as much as the weight of C-14 enol ether (7). The temperature for hydrolysis is from 10° C. to 35° C., and gas chromatography is used for tracking the reaction.

In the invention, a method for refining the crude product of 2-pos double bond C-14 aldehyde (3) is found by accident, comprising the following refining steps: a) crude product of C-14 aldehyde reacts with sodium bisulfate aqueous solution to obtain an adduct, i.e. sodium bisulfite salt, and excessive amount of sodium bisulfite is used to guarantee smooth salt forming reaction; 2) layering is performed upon sufficient salt forming, an organic solvent is used for extracting an aqueous layer to remove residual organic impurities, and the product sodium bisulfite salt is contained in the aqueous layer for future use; c) the aqueous layer and the organic solvent are stirred together, sodium carbonate or base is added in batches for treatment, or the aqueous layer is firstly treated with sodium carbonate or base and then added with the organic solvent for extraction; the amount of the sodium carbonate or the base is more than that of the sodium bisulfite in the step a) to guarantee the complete dissociation of sodium bisulfite salt; and d) layering is performed, the resultant organic layer is water-rinsed and dried, and the solvent is removed by distillation to obtain pure 2-pos double bond C-14 aldehyde.

The organic solvent used in the salt forming and dissociation reactions is methylene dichloride, cyclohexane or methylbenzene, and the temperature is from 10° C. to 40° C.

Typically, preparation of adduct from aldehyde and sodium bisulfite and then hydrolysis is the common purification method for aldehydes. In the invention, after such treatments, aldehyde is purified by removing other organic impurities in a way of separation; besides, 3-pos double bond C-14 aldehyde (3A) can also be directly rearranged as 2-pos double bond C-14 aldehyde (3), and the mechanism is as follows:

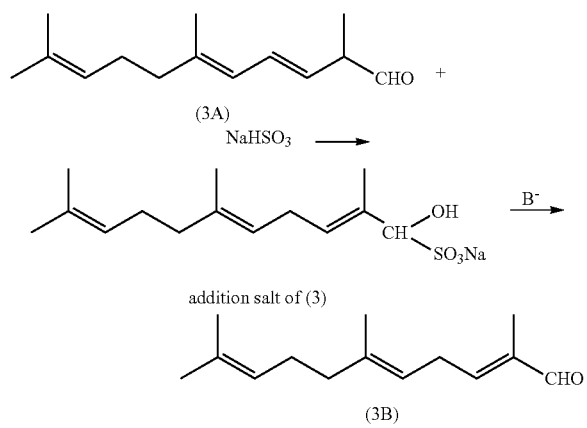

That is to say, double bond migration has occurred at the time of addition, and the driving force is the double bond migration caused by anion stabilization during the addition of aldehyde group and bisulfite. After such treatments, the rearranged target product 2-pos double bond C-14 aldehyde (3) is obtained, and the purification effect is achieved, the purity of product is quite high after simple removal of solvent by distillation, thus the requirements in the next reaction can be met; however, the current common purification method has no purification effect, so rectification is indispensable.

As discussed above, the invention can obtain the key intermediate of lycopene, i.e. 2-pos double bond C-14 aldehyde (3), from the raw material citral (5) only by two reactions (condensation, hydrolysis), so the invention has the advantages of simple and convenient process route, easily available raw materials, low cost and great industrial value.

2-pos double bond C-14 aldehyde (3) and tetraethyl methylenediphosphonate are subjected to Wittig-Horner condensation reaction to prepare 1,3,6,10-tetra-double bond pentadec-carbon phosphonate (4), and 1,3,6,10-tetra-double bond pentadec-carbon phosphonate (4) and decadialdehyde are subjected to condensation reaction to obtain lycopene (1), and specific synthesis method can be seen in related documents, so detailed description is unnecessary (application number: 20101020583.3).

It shall be noted that, the raw material citral is a cis-trans isomer mixture, so the condensation product C-14 enol ether (7), the hydrolysis product 2-pos double bond C-14 aldehyde (3) and 1,3,6,10-tetra-double bond pentadec-carbon phosphonate (4) are all cis-trans isomer mixtures; however, the cis-trans isomers contained in these intermediates have no impact on the all-trans structure of the final product lycopene (1), this is because the final product all-trans lycopene can be obtained only after the crude product of lycopene is subjected to cis-trans isomerism purification.

Further description is made below to the invention with reference to the embodiments.

DETAILED DESCRIPTION OF THE EMBODIMENTS

The analysis instruments and equipment used in the embodiments are as follows: gas chromatography-mass spectrometry MS5973N-GC6890N (Agilent Technologies); nuclear magnetic resonance instrument, AVANCE DMX 400M (TMS Internal Label); infrared spectrometer, NICOLET 360FT-IR; and gas chromatography, SHANGHAI TECHCOMP 7890F.

Embodiment 1: Preparation of C-14 enol ether (7)

12.3 g potassium tert-butoxide (0.11 mol) and 50 ml mixture of tetrahydrofuran and dimethyl sulfoxide based on a ratio of 8:1 (volume ratio) are added to a 250 ml three-necked bottle under the protection of nitrogen, the temperature of cold bath is maintained, 22.2 g C-4 phosphate ester (6) (0.1 mol) is dropwise added under mechanical stirring, the addition can be finished about half an hour later while the temperature is maintained at −30° C. to −25° C., and stirring is continued for about 1 hour while the temperature is maintained, so that sufficient dissociation reaction of carbanions is realized; afterwards, 15.2 g citral (5) (0.1 mol, cis-trans mixture) is dropwise added while the temperature is maintained at −30° C. to −25° C., the addition can be finished about 1 hour later, stirring is continued for about half an hour while the temperature is maintained, gas chromatography is used for tracking the reaction, 50 ml water and 100 ml ether are added and stirred for 10 minutes, layering is performed, the ether layer is rinsed by sodium chloride aqueous solution with the concentration of 5% 3 times (25 ml for each time), the organic layer is dried by magnesium sulfate and filtered, the solvent in filtrate is removed by distillation under reduced pressure to obtain crude product, the residues are distilled under reduced pressure to obtain 12.8 g 97-101° C./1 mmHg fraction, which is transparent liquid, there are four peaks with similar sizes in product according to GC analysis, the total content is 93.5% and the yield is 54.5%. The four products are 1-pos methoxyl cis-trans isomers and 5,6-pos double bond cis-trans isomers respectively.

Structural Confirmation of Products (1-methoxyl cis-trans; 5,6-double bond cis):

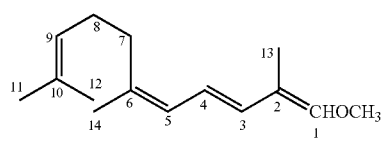

GC-MS (m/e): 220, 205, 188, 175, 151, 145, 135, 119, 109, 105, 91(100%), 85, 79, 69, 59, 53, 45, 41;

Structural Confirmation of Products (1-methoxyl cis-trans; 5,6-double bond trans):

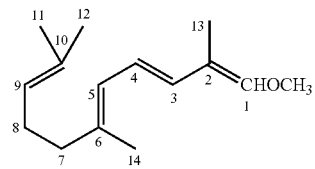

GC-MS (m/e): 220, 151(100%), 136, 119, 105, 91, 85, 77, 69, 65, 59, 53, 45.

$^1$HNMR(δ, ppm, 400 MHz, CDCl$_3$): 1.606(s, 3H, C13-H), 1.685(s, 6H, C11-H, C12-H),1.782(s, 3H, C14-H), 2.049-2.171(m, 4H, C7-H, C8-H), 3.619(s, 3H,O—CH$_3$), 5.057-5.164(m, 1H, C9-H), 5.870(s, 1H, C1-H), 5.940(dd, J=11.2

Hz, 5.6 Hz 1H, C4-H), 6.287(dd, J=15.2 Hz, 11.2 Hz 1H, C5-H), 6.625(dd, J=15.2 Hz, 12.4 Hz 1H, C3-H);

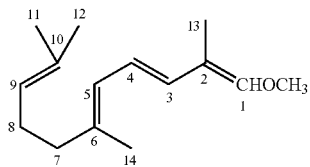

$^{13}$CNMR(δ, ppm, 400 MHz, CDCl$_3$): 144.91, 144.85(C1); 138.03, 137.76(C6, trans); 131.85, 131.61(C6 cis); 129.04, 128.24(C10); 126.68, 125.22(C3); 125.88, 125.53(C9); 124.15, 124.09(C4); 123.24, 123.14(C5); 112.80(C2); 59.78 (O—CH$_3$); 40.10(C7 cis); 32.68(C8 cis); 26.68, 26.67 (C7 trans, C8 trans); 25.71(C11); 24.01(C14 cis); 17.63(C12); 16.81(C14 trans); 14.49(C13).

DEPT135: 144.91, 144.85, 126.68, 125.22; 125.88, 125.53; 124.15, 124.09; 123.24, 123.14; 59.78; 40.10(D); 32.68(D); 26.86, 26.67(D); 25.71; 24.01; 17.63; 16.81; 14.49.

Embodiments 2-8: Preparation of C-14 enol ether (7) by Condensation Reaction Under Different Base, Solvent and Temperature Conditions A fixed amount of base and 20 ml certain solvent (see the table below for the type of base and solvent) are added to a 250 ml three-necked bottle under the protection of nitrogen, the temperature of cold bath is maintained, 20 ml certain solvent (the same as the solvent above) with a fixed amount of C-4 phosphate ester (6) (see the table below for molar weight) dissolved therein is dropwise added under mechanical stirring, the addition can be finished about half an hour later while a particular temperature is maintained, and stirring is continued for about 1 hour while the temperature is maintained, so that sufficient dissociation reaction of carbanions is realized; afterwards, a solvent (the same as the solvent above) with 7.6 g citral (5) (0.05 mol, cis-trans mixture) dissolved therein is dropwise added while the temperature above is maintained, the addition can be finished about 1 hour later, stirring is continued for half an hour while the temperature is maintained, gas chromatography is used for tracking the reaction, 30 ml water and 50 ml ether are added and stirred for 10 minutes, layering is performed, the ether layer is rinsed by 15 ml sodium chloride aqueous solution with the concentration of 5%, dried by magnesium sulfate and filtered, the solvent in filtrate is removed by distillation under reduced pressure to obtain crude product, the residues are distilled under reduced pressure to collect 97-101° C./1 mmHg fraction, the GC content is measured, the yield is calculated, and the results are shown in the table below.

TABLE 1

Potassium tert-butoxide, tetrahydrofuran and dimethyl sulfoxide are replaced by different bases and solvents and the amount of base is adjusted, the results are shown in the table below: (Note: n-butyl lithium is 2.5 mol/l n-hexane solution)

| Embodiment | Type of Base | Amount of Base (Mol) | Solvent | Amount of C-4 Phosphate Ester (Mol) | Reaction Temperature (° C.) | Amount of Obtained Product (g) and Product Content (%) | Yield (%) |
|---|---|---|---|---|---|---|---|
| 2 | sodium ethoxide | 0.06 | methylbenzene | 0.050 | 5 | 6.0; 91.2 | 49.7 |
| 3 | sodium tert-butoxide | 0.05 | ethylene glycol dimethyl ether | 0.045 | −10 | 7.2; 91.5 | 59.8 |
| 4 | potassium tert-butoxide | 0.055 | dimethyl formamide | 0.048 | −20 | 9.0; 92.3 | 75.5 |
| 5 | n-butyl lithium | 0.051 | tetrahydrofuran/n-hexane | 0.050 | −40 | 9.1; 93.6 | 77.4 |
| 6 | sodium methoxide | 0.052 | ether | 0.055 | 15 | 3.7; 89.9 | 30.2 |
| 7 | potassium tert-butoxide | 0.054 | dimethyl sulfoxide | 0.060 | 20 | 7.4; 91.3 | 61.4 |
| 8 | potassium tert-butoxide | 0.054 | hexamethylphosphoric triamide | 0.056 | 30 | 6.7; 91.4 | 58.4 |

The products obtained are mixed to obtain 49 g crude product of enol ether, which is used for the experiments under the condition of hydrolysis in the embodiments 10 to 16 below.

Embodiment 9: Preparation of C-14 aldehyde by Hydrolysis of C-14 enol ether (7)

11.0 g C-14 enol ether (7) (0.05 mol) prepared in the embodiment 1, 100 g solvent tetrahydrofuran and 1.5 g para-toluenesulfonic acid are added to a 250 ml three-necked bottle under the protection of nitrogen and are then uniformly stirred, afterwards, 22 g water is dropwise added for reaction for 1 day under stirring and at the temperature from 20° C. to 25° C.; after the reaction is basically completed according to the tracking of gas chromatography, solution prepared from 2 g sodium bicarbonate and 20 ml water is added for neutralization, tetrahydrofuran is distilled out under reduced pressure by a water pump and then 100 ml cyclohexane is added, layering is performed, the organic layer is rinsed by 30 ml water and dried by anhydrous magnesium sulfate, afterwards, the solvent is recovered under reduced pressure to obtain 9.5 g crude product of C-14 aldehyde, and according to GC analysis, the product is a mixture containing a fixed amount of 3-pos double bond C-14 aldehyde (3A) and a fixed amount of 2-pos double bond C-14 aldehyde (3), and its total content is 77%; the mixture is added with 9.5 g sodium bisulfate, then dissolved in 80 ml aqueous solution and magnetically stirred for 120 minutes under the protection of nitrogen to result in substantial removal of organic matters; 20 ml cyclohexane is added and stirred for 15 minutes, and layering is then performed; the aqueous layer is added with 80 ml cyclohexane and then added with 12 g potassium carbonate under stirring to acquire alkality, and these additions are followed by stirring for 10 minutes and layering; the organic layer is then rinsed by 20 ml sodium chloride aqueous solution with the concentration of 10%, dried by magnesium sulfate and filtered, the solvent is dried by distillation under reduced pressure to obtain 7.8 g pure 2-pos double bond C-14 aldehyde, and the product has the content of 93.1% and the yield of 70.5% according to GC analysis.

Structural Confirmation of Products (1-methoxyl cis-trans; 5,6-double bond cis):

GC-MS (m/e): 206, 191, 177, 163, 150, 135, 123, 109, 95, 81, 69(100%), 53, 41 29;

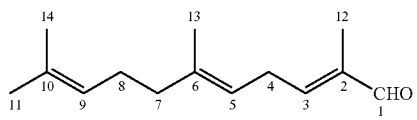

$^1$HNMR($\delta$, ppm, 400 MHz, CDCl$_3$): 1.07(t, J=7.2 Hz, 3H, C$_{12}$—H), 1.17(d, J=6.8 Hz, 3H, C$_{13}$—H), 1.33(t, J=6.8 Hz, 3H, C$_{11}$—H, C$_{14}$—H), 2.18-2.33(m, 4H, C$_8$—H, C$_7$—H), 2.53-2.60(M, 2H, C$_4$—H), 5.09-5.11(m, 1H, C$_9$—H), 5.47-5.52(m, 1H, C$_5$—H), 6.52(t, J=6.4 Hz, 1H, C$_3$—H), 9.69(s, 1H, —CHO).

Embodiments 10-16: Preparation of C-14 aldehyde by Hydrolysis of enol ether (7) Under Different Conditions 5.5 g C-14 enol ether (7) (0.025 mol) prepared in the embodiments 2-8, a fixed amount of solvent and a fixed amount of catalyst (see the table below for molar weight) are added to a 250 ml three-necked bottle under the protection of nitrogen and are then uniformly stirred, afterwards, a fixed amount of water is dropwise added for reaction under stirring at a particular temperature; after the reaction is basically completed according to the tracking of gas chromatography, solution prepared from 1.5 g sodium bicarbonate and 15 ml water is added for neutralization, the solvent is distilled out under reduced pressure by a water pump and then 50 ml cyclohexane is added, layering is performed, the organic layer is rinsed by 20 ml water and dried by anhydrous magnesium sulfate, afterwards, the solvent is recovered under reduced pressure to obtain crude product of C-14 aldehyde; the GC content is measured, the yield is calculated, and the results are shown in the table below.

TABLE 2

Different acid catalysts and solvents are adopted and the amount of acid and water is adjusted, the results are shown in the table below:

| Embodiment | Type of Acid | Amount of Acid (Weight) | Solvent and Amount (ml) | Amount of Water (Weight) | Reaction Temperature (°C.) | Amount of Obtained Product (g) and Product Content (%) | Yield (%) |
|---|---|---|---|---|---|---|---|
| 10 | sulfuric acid | 0.025 | tetrahydrofuran, 25 | 5.0 | 15 | 3.3; 65.5 | 42.0 |
| 11 | sulfuric acid | 0.045 | acetone, 30 | 6.0 | 10 | 4.3; 72.1 | 60.2 |
| 12 | trifluoroacetic acid | 0.055 | tetrahydrofuran, 55 | 20.0 | 20 | 5.3; 75.3 | 79.0 |
| 13 | trifluoroacetic acid | 0.050 | acetone, 45 | 15.5 | 30 | 5.5; 73.5 | 78.5 |
| 14 | paratoluenesulfonic acid | 0.030 | tetrahydrofuran, 35 | 12.0 | 15 | 5.8; 71.8 | 80.9 |
| 15 | paratoluenesulfonic acid | 0.040 | acetone, 40 | 12.0 | 25 | 5.7; 76.1 | 84.2 |
| 16 | aminosulfonic acid | 0.025 | tetrahydrofuran, 25 | 8.0 | 30 | 5.5; 79.4 | 84.8 |

35.4 g crude products of C-14 aldehyde derived from the above experiments under various conditions are mixed, the mixture is added with 55 g sodium bisulfate, then dissolved in 400 ml aqueous solution and magnetically stirred for 120 minutes under the protection of nitrogen to result in substantial removal of organic matters; 100 ml cyclohexane is added and stirred for 5 minutes, and layering is then performed; the aqueous layer is added with 300 ml cyclohexane and then added with 60 g potassium carbonate under stirring to acquire alkality, and these additions are followed by stirring for 40 minutes and layering; the organic layer is then rinsed by 50 ml sodium chloride aqueous solution with the concentration of 10%, dried by magnesium sulfate and filtered, the solvent is dried by distillation under reduced pressure to obtain 25.5 g pure 2-pos double bond C-14 aldehyde (3). According to GC analysis, the product has the content of 93.1% and the total yield of 65.7% in the case of hydrolysis seven times.

Embodiment 17: Preparation of 1,3,6,10-tetra-double bond pentadec-carbon diethyl phosphonate (4) (3,7,11-trimethyl-1,3,6,10-tetraene-dodecyl diethyl phosphonate)

1.1 g (0.0275 mol) sodium hydride (60% content) is added to a 100 ml three-necked bottle under the protection of nitrogen, paraffin oil is removed by rinsing twice with 10 ml n-hexane each time; then, 10 ml methylbenzene is added, 8.6 g tetraethyl methylenediphosphonate (0.03 mol) is dropwise added to 20 ml methylbenzene solution under magnetic stirring, the temperature of cold water bath is maintained at 10 to 15° C. while addition, a large amount of gas is discharged, the addition can be finished about half an hour later, and stirring is continued for reaction for half an hour; afterwards, 5.1 g 2-pos double bond C-14 aldehyde (3) (prepared in the embodiment 9, 0.025 mol) is dropwise added and dissolved in 20 ml methylbenzene solution, the temperature of cold water bath is maintained at 10 to 15° C. while addition, the addition can be finished about half an hour later, and stirring is continued for reaction for half an hour. 20 ml water is added to the reaction mixture solution, which is followed by stirring for 10 minutes and layering, the organic layer is rinsed by 20 ml sodium hydride aqueous solution with the concentration of 10%, dried by magnesium sulfate and filtered, and the solvent is dried by distillation under reduced pressure to obtain 7.5 g crude product of 1,3,6,10-tetra-double bond pentadec-carbon phosphonate (4), which is light brown liquid and has the GC content of 93.2% and the yield of 88.5%.

Structural Confirmation:

GC-MS (m/e): 340, 325, 284, 271, 243, 217(100%), 205, 192, 159, 105, 79

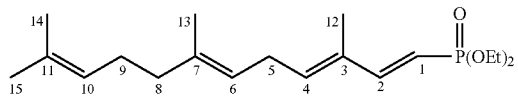

$^1$HNMR($\delta$, ppm, 400 MHz, CDCl$_3$): 7.095(dd, J=17.2 Hz, 4.8 Hz, 1H, C2-H), 6.643-6.699(m, 1H, C4-H), 5.823(t, J=4.8 Hz, 1H, C6-H), 5.605(t, J=17.6 Hz, 1H, C1-H), 5.602-5.7141 (m, 1H, C10-H), 4.023-4.095(m, 4H, O—C*H$_2$—CH$_3$), 2.614-2.729(m, 1H, C5-H), 2.272-2.522(m, 4H, C8-H and C9-H), 1.781(s, 3H, C13-H), 1.686(s, 3H, C14-H), 1.609(s, 3H, C15-H), 1.313(t, J=7.2 Hz, 6H, O—CH2-C*H3), 0.854 (d, J=6.8 Hz, 3H, C12-H).

Embodiment 18: Preparation of Lycopene from 1,3,6,10-tetra-double bond pentadec-carbon diethyl phosphonate (4)

6.8 g (0.02 mol) 1,3,6,10-tetra-double bond pentadec-carbon phosphonate (4) prepared in the embodiment 17 and 30 ml mixture of tetrahydrofuran and dimethyl sulfoxide based on a ratio of 8:1 (volume ratio) are added to a 250 ml three-necked bottle under the protection of nitrogen, 2.3 g (0.021 mol) potassium tert-butoxide is added at about 5° C. (ice water bath) under mechanical stirring, stirring is performed for 2 hours while the temperature is maintained, then 1.6 g decadialdehyde (8) (0.0098 mol) is dropwise added to 10 ml mixture of tetrahydrofuran and dimethyl sulfoxide based on a ratio of 8:1 (volume ratio) (for the preparation of 8, see Embodiment XIV in U.S. Pat. No. 5,061,819), the addition can be finished about 20 minutes later, stirring is continued for 15 minutes while the temperature is maintained, and the temperature then rises to a range from 20-25° C. for reaction for 1 hour. Addition of 100 ml chloroform upon complete reaction is followed by rinsing three times with sodium hydride aqueous solution with the concentration of 10% (75 ml for each time), the organic layer is dried by magnesium sulfate and filtered, the filtrate is refluxed and rearranged for 2 hours under the protection of nitrogen and the solvent is then removed by distillation under reduced pressure to obtain crude product, and the crude product is re-crystallized with 30 ml methylene dichloride to obtain 2.8 g (the yield is 52.3%) product.

Structural Confirmation $^1$HNMR($\delta$, ppm, 400 MHz, CDCl$_3$): $\delta$ 5.111, 5.975-6.943 (m, 8H, double bond H), 5.11(m, 1H), 1.552(S, 6H), 1.616(S, 3H), 1.689(S, 3H), 2.129(S, 3H), 1.427-2.212(m, 4H)

$^{13}$CNMR(400 MHz, CDCl$_3$) $\delta$(ppm): 139.52(C5); 137.37 (C12); 136.56(C13); 136.19(C9); 135.42(C10); 132.66(C14); 131.76(C1); 131.58(C8); 130.09(C15); 125.73 (C11); 125.17(C2); 124.82(C6); 123.96(C7); 40.25(C4); 26.69(C3); 25.72(C20); 18.42(C19); 16.97(C18); 12.91(C17); 12.81(C16)

There are 13 peaks between $\delta$(ppm)120 and $\delta$(ppm)140; there are 7 peaks between $\delta$(ppm)10 and $\delta$(ppm)45, thus determining the all-trans structure and high purity of product.

DEPT135: 137.37; 135.42; 132.66; 131.58; 130.09; 125.73; 125.17; 124.82; 123.96; 58.48(D); 40.25(D); 26.69 (D); 25.72; 18.42; 16.97; 12.91; 12.81.

What is claimed is:

1. 1-methoxyl-2,6,10-trimethyl-1,3,5,9-undec-tetraene, C-14 enol ether for short, having the structural formula below:

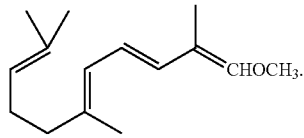

2. A preparation method of the C-14 enol ether according to claim 1, comprising the following steps:

1) C-4 phosphate ester, shown as Formula (6), is subjected to rearrangement dissociation reaction under the protection of inert gas and at the presence of organic solvent and base, wherein the reaction temperature is from −40° C. to 30° C.;

2) citral, shown as Formula (5), is then added to the substance derived from the step 1) to perform Wittig-Horner condensation reaction at the presence of base and organic solvent in order to obtain C-14 enol ether shown as Formula (7), wherein the reaction temperature is from −40° C. to 30° C. and the synthetic route is as follows:

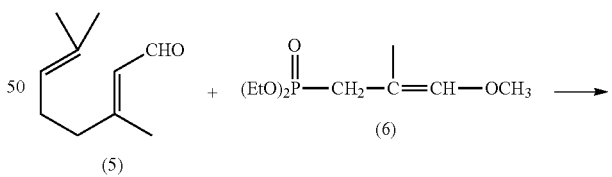

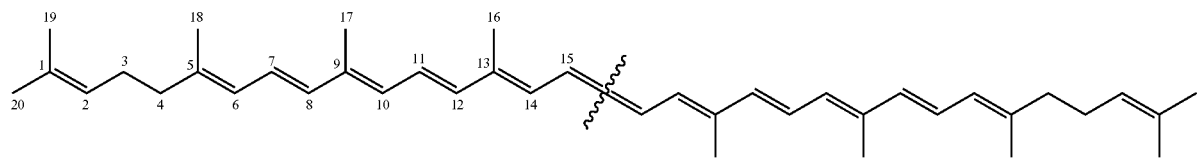

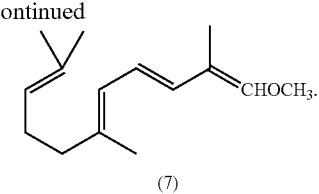

(7)

3. The preparation method according to claim 2, characterized in that the base used is organic strong base, and the organic solvent is any of or the mixture of more than two of ether solvent, dipolar aprotic solvent, aromatic hydrocarbon solvent and alkane solvent.

4. The preparation method according to claim 3, characterized in that the ether solvent is ether, tetrahydrofuran or ethylene glycol dimethyl ether; the dipolar aprotic solvent is dimethyl formamide, dimethyl sulfoxide or hexamethylphosphoric triamide; the aromatic hydrocarbon solvent is methylbenzene; and the alkane solvent is n-hexane.

5. The preparation method according to claim 2, characterized in that, upon the completion of condensation reaction, water and organic solvent are added for the purpose of layering, a byproduct, i.e. diethyl phosphate sodium salt, is dissolved in water and a product, i.e. C-14 enol ether, exists in organic phase, and the target product, i.e. C-14 enol ether, can be obtained by removing the organic solvent in a manner of organic phase distillation.

6. A method for preparing lycopene intermediate 2-pos double bond C-14 aldehyde from the C-14 enol ether according to claim 1, comprising the following steps:
step 1), C-14 enol ether, acid catalyst, water and homogeneous phase solvent are mixed for hydrolysis under the protection of nitrogen in order to obtain a crude mixture containing 2-pos double bond C-14 aldehyde (3) and 3-position double bond C-14 aldehyde (3A), and the reaction route is as follows:

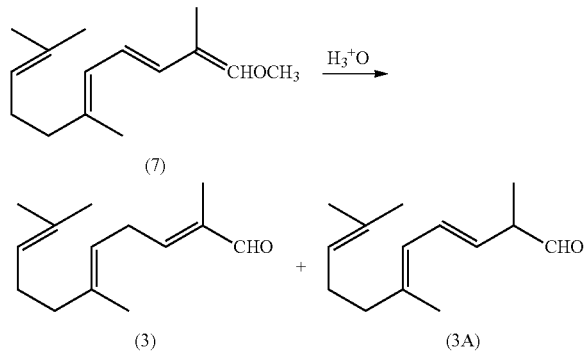

step 2), upon the completion of hydrolysis, sodium bicarbonate aqueous solution is firstly added to adjust the reaction system to be neutral, solvent is then distilled out under reduced pressure, a water-immiscible organic solvent is added for extraction, layering is performed and crude product of C-14 aldehyde is then obtained by drying the solvent by distillation at organic layer, and pure 2-pos double bond C-14 aldehyde is prepared by refining the crude product of C-14 aldehyde.

7. The method according to claim 6, characterized in that the acid catalyst is sulfuric acid, p-toluenesulfonic acid, trifluoroacetic acid or aminosulfonic acid, and the amount of the acid catalyst is 5-10% of the weight of C-14 enol ether; the homogeneous phase solvent is tetrahydrofuran or acetone, and the addition amount of the homogeneous phase solvent is 5-10 times as much as the weight of C-14 enol ether; the amount of water is 1-3 times as much as the weight of C-14 enol ether; and the temperature for hydrolysis is from 10° C. to 35° C.

8. The method according to claim 6, characterized in that the refining step is as follows: a) crude product of C-14 aldehyde reacts with sodium bisulfite aqueous solution to obtain an adduct, i.e. sodium bisulfite salt, and excessive amount of sodium bisulfite is used to guarantee smooth salt forming reaction; 2) layering is performed upon sufficient salt forming, an organic solvent is used for extracting an aqueous layer to remove residual organic impurities, and the product sodium bisulfite salt is contained in the aqueous layer for future use; c) the aqueous layer and the organic solvent are stirred together, sodium carbonate or other base is added in batches for treatment, or the aqueous layer is firstly treated with sodium carbonate or other base and then added with the organic solvent for extraction; the amount of the sodium carbonate or the base is more than that of the sodium bisulfite in the step a) to guarantee the complete dissociation of sodium bisulfite salt; and d) layering is performed, the resultant organic layer is water-rinsed and dried, and solvent is removed by distillation to obtain pure 2-pos double bond C-14 aldehyde.

9. The method according to claim 8, characterized in that the organic solvent used in the salt forming and dissociation reactions is methylene dichloride, cyclohexane or methylbenzene.

10. The method according to claim 8, characterized in that the temperature for the salt forming and dissociation reactions is from 10° C. to 40° C.

11. The method according to claim 7, characterized in that the refining step is as follows: a) crude product of C-14 aldehyde reacts with sodium bisulfite aqueous solution to obtain an adduct, i.e. sodium bisulfite salt, and excessive amount of sodium bisulfite is used to guarantee smooth salt forming reaction; 2) layering is performed upon sufficient salt forming, an organic solvent is used for extracting an aqueous layer to remove residual organic impurities, and the product sodium bisulfite salt is contained in the aqueous layer for future use; c) the aqueous layer and the organic solvent are stirred together, sodium carbonate or other base is added in batches for treatment, or the aqueous layer is firstly treated with sodium carbonate or other base and then added with the organic solvent for extraction; the amount of the sodium carbonate or the base is more than that of the sodium bisulfite in the step a) to guarantee the complete dissociation of sodium bisulfite salt; and d) layering is performed, the resultant organic layer is water-rinsed and dried, and solvent is removed by distillation to obtain pure 2-pos double bond C-14 aldehyde.

12. The method according to claim 11, characterized in that the organic solvent used in the salt forming and dissociation reactions is methylene dichloride, cyclohexane or methylbenzene.

13. The method according to claim 11, characterized in that the temperature for the salt forming and dissociation reactions is from 10° C. to 40° C.

* * * * *